(12) United States Patent
Le et al.

(10) Patent No.: US 10,980,932 B2
(45) Date of Patent: Apr. 20, 2021

(54) METHODS FOR THERAPEUTIC TARGETING OF CIRCULATING TUMOR CELLS DURING HEMODIALYSIS

(71) Applicant: ROSEMAN UNIVERSITY OF HEALTH SCIENCES, Las Vegas, NV (US)

(72) Inventors: Thuc T. Le, Las Vegas, NV (US); Ranjana Mitra, Las Vegas, NV (US); Yasuyo Urasaki, Las Vegas, NV (US); Oscar B. Goodman, Las Vegas, NV (US)

(73) Assignee: Roseman University of Health Sciences, Las Vegas, NV (US)

( * ) Notice: Subject to any disclaimer, the term of this patent is extended or adjusted under 35 U.S.C. 154(b) by 544 days.

(21) Appl. No.: 15/570,032

(22) PCT Filed: Feb. 26, 2016

(86) PCT No.: PCT/US2016/019793
§ 371 (c)(1),
(2) Date: Oct. 27, 2017

(87) PCT Pub. No.: WO2016/175913
PCT Pub. Date: Nov. 3, 2016

(65) Prior Publication Data
US 2018/0104403 A1    Apr. 19, 2018

Related U.S. Application Data

(60) Provisional application No. 62/153,139, filed on Apr. 27, 2015.

(51) Int. Cl.
*A61M 1/36* (2006.01)
*A61M 1/16* (2006.01)
*A61M 1/30* (2006.01)
*A61P 35/00* (2006.01)
*A61M 1/38* (2006.01)
*A61K 31/713* (2006.01)
*A61M 1/34* (2006.01)

(52) U.S. Cl.
CPC ......... *A61M 1/3687* (2013.01); *A61K 31/713* (2013.01); *A61M 1/16* (2013.01); *A61M 1/301* (2014.02); *A61M 1/3615* (2014.02); *A61M 1/38* (2013.01); *A61P 35/00* (2018.01); *A61M 1/34* (2013.01); *A61M 2205/054* (2013.01); *C12N 2310/14* (2013.01)

(58) Field of Classification Search
CPC ........ A61M 1/16; A61M 1/3615; A61M 1/38; A61M 1/3687; A61M 2205/054
See application file for complete search history.

(56) References Cited

U.S. PATENT DOCUMENTS

2013/0131423 A1    5/2013   Wang et al.
2013/0261683 A1*  10/2013   Soikum ................. C12N 13/00
                                                                   607/2

OTHER PUBLICATIONS

Zhou W, Xiong Z, Liu Y, Yao C, Li C. Low voltage irreversible electroporation induced apoptosis in HeLa cells.J Can Res Ther 2012;8:80-85 (Year: 2012).*

(Continued)

*Primary Examiner* — Leslie R Deak
(74) *Attorney, Agent, or Firm* — Hogan Lovells US LLP

(57) ABSTRACT

The present invention is directed towards methods for therapeutically targeting circulating tumor cells during hemodialysis.

10 Claims, 12 Drawing Sheets

(56) References Cited

OTHER PUBLICATIONS

International Search Report received in PCT Application No. PCT/US2016/019793, dated May 16, 2016; 3 pages.
Mitra et al., "Abstract 554: Detection and separation of live circulating tumor cells using lipid dye." Cancer Research. Aug. 1, 2015;75:554. Proceedings: AACR 106th Annual Meeting 2015: Apr. 18-22; Philadelphia, PA; 1 page.

* cited by examiner

Figure 1. Lipid-rich CTCs isolated from the peripheral blood of breast, bladder, prostate, and skin cancer patients. Images were taken with coherent anti-Stokes Raman scattering (CARS) microscopy at 2851 cm$^{-1}$ to probe for $CH_2$ vibration.

Figure 2. 2D Western blots of protein lysine acetylation profiles. Protein lysine acetylation profiles of (A) untreated LNCaP cells, (B) LNCaP cells incubated with human plasma, (C) untreated RWPE1 cells, and (D) RWPE1 cells incubated with human plasma.

FIG. 3

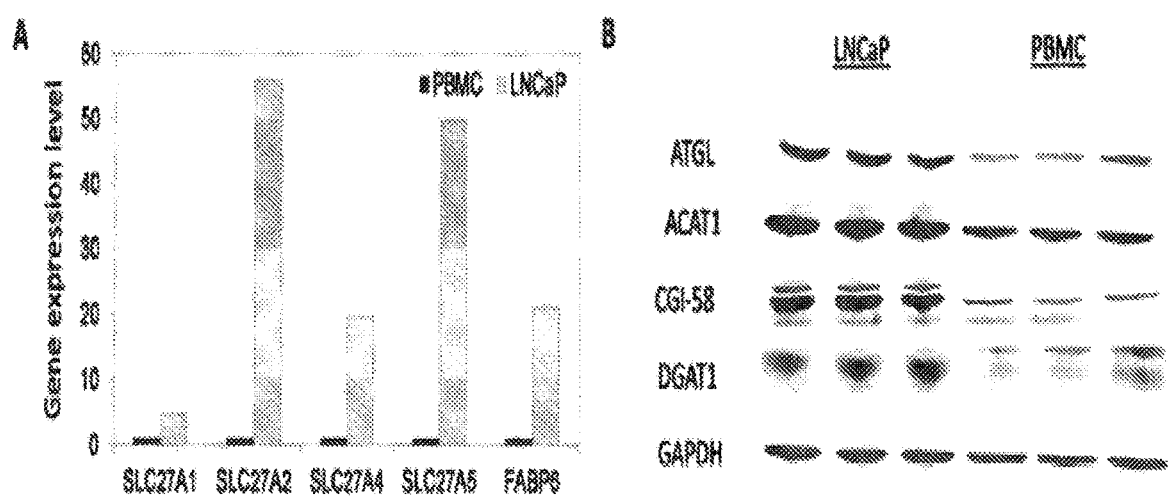

Figure 3. Elevated expression of lipid metabolism proteins in LNCaP prostate cancer cells compared to peripheral mononucleated blood cells (PBMC). (A) Gene expression levels of fatty acid transport proteins (SLC27A1, 2, 4, 5) and fatty acid binding protein (FABP6). (B) Protein expression levels of adipose triglyceride lipase (ATGL), acetyl-CoA acetyltransferase (ACAT1), 1-acylglycerol-3-phosphate O-acyltransferase (CGI-58), diglyceride acyltransferase 1 (DGAT1).

FIG. 4

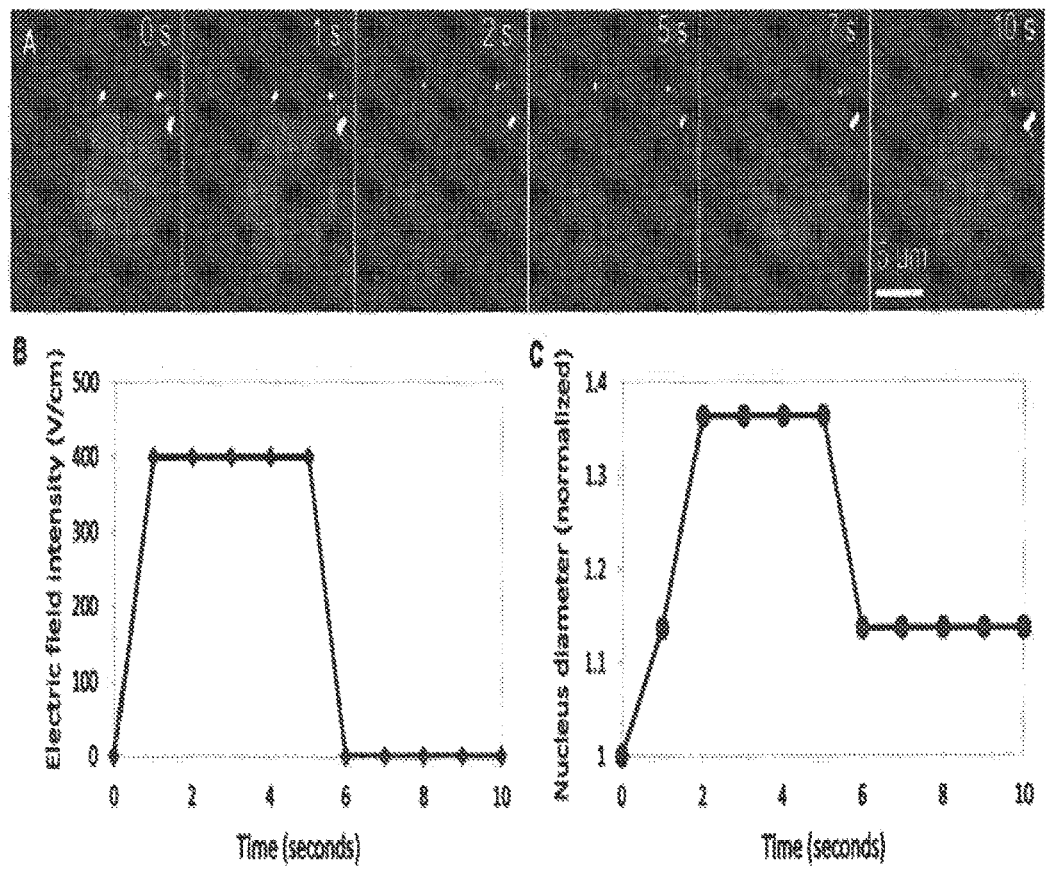

Figure 4. Nucleus expansion of a lung cancer cell under an applied electric field. (A) Time-lapse images of simultaneous CARS imaging of a cancer cell membrane (red) and two-photon fluorescence imaging of Hoechst 33342-stained nucleus (blue). The nucleus (blue) expanded and retracted as a function of electric field intensity shown in (B). (B) Electric field intensity as a function of time. (C) Normalized nucleus diameter of a cancer cell shown in (A) as a function of electric filed intensity shown in (B) over time.

FIG. 5

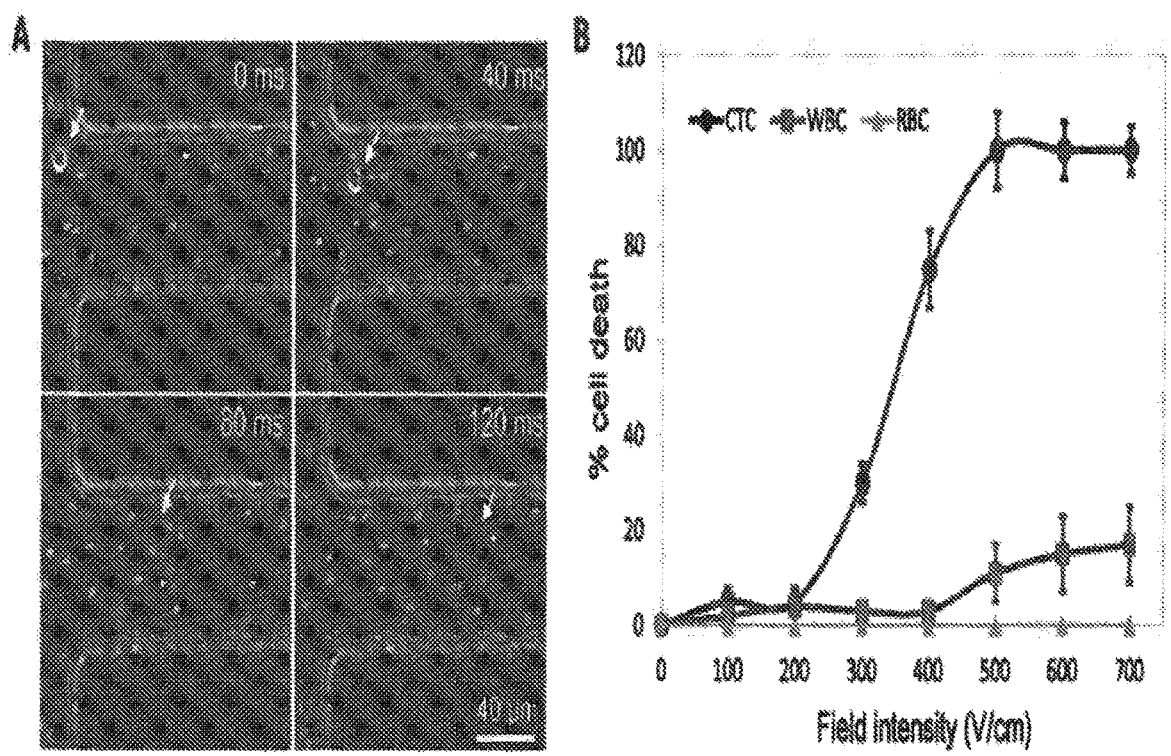

Figure 5. Selective killing of lung CTC in whole blood samples with applied electric fields. (A) A lung CTC (arrow) expanded rapidly in a microfluidic channel with electric field intensity of 400 V/cm. No significant expansion of white blood cells or red blood cells was observed. (B) Percentage cell death as a function of applied electric field intensity. White blood cells (WBC), red blood cells (RBC). Error bars are standard deviation across triplicate experiments.

Figure 6. Therapeutic targeting of CTC during hemodialysis. Schematic of the extracorporeal CTC targeting apparatus is shown. CTC in extracorporeal blood are exposed to drugs (therapeutic agents) and localized electric fields. Excess drugs are removed from blood via dialysis prior to clean blood being returned to patients.

Figure 7. Toxicity of plasma to metastatic prostate cancer LNCaP cells. Incubation with 50% plasma for 24 hours lead to a reduction of nearly 60% in cell viability. Error bars are standard deviation of triplicate experiments. Cell viability was determined using commercial MTS assays according to manufacturer's protocols.

Figure 8. siRNA targeting of lipid metabolism proteins reduces LNCaP viability. LNCaP viability as a function of siRNA targeting ATGL, DGAT1, ACAT1, and CGI-58 in growth media (A) or growth media supplemented with 50% plasma (B). Error bars are standard deviation of triplicate experiments.

Figure 9. siRNA targeting of lipid metabolism proteins has minimal effect on PBMC viability. Graphical representation of PBMC viability as a function of siRNA targeting of ATGL, DGAT1, ACTA1, and CGI-58. Error bars are standard deviation of triplicate experiments.

Figure 10. Uridine and glucosamine promote protein glycosylation and suppress protein acetylation.

Figure 11. Post-translational modifications cocktail reduces LNCaP viability in the absence or presence of plasma. Error bars are standard deviation of triplicate experiments.

Figure 12. PTM cocktail enhances PBMC viability. Error bars are standard deviation of triplicate experiments.

METHODS FOR THERAPEUTIC TARGETING OF CIRCULATING TUMOR CELLS DURING HEMODIALYSIS

CROSS-REFERENCE TO RELATED APPLICATION

This application claims the benefit of U.S. Provisional Application No. 62/153,139, filed Apr. 27, 2015 the entire disclosure of which is hereby incorporated by reference herein.

DESCRIPTION

Technical Field

The present invention is directed to methods for therapeutic targeting of circulating tumor cells ("CTCs") during hemodialysis. In particular, the present invention is directed to a method for detecting and reducing the viability of circulating tumor cells with chemotherapeutic agents during hemodialysis.

Background of the Invention

Development of metastasis in vital organs remains the major cause of cancer-related mortality. During tumor development, malignant cells gain the ability to enter the vasculature, circulate, adhere to endothelial cells, extravasate and grow in distant organs. Circulating tumor cells ("CTCs") are cells that have detached from a primary tumor and circulate in the bloodstream. CTCs provide the link between the primary and metastatic tumors. Detection of CTCs in peripheral blood provides important diagnostic information across a broad range of epithelial cancers, such as prostate, breast and colon cancer. CTC assays also have predictive value that can guide treatment selection and protocols. For instance, the number of CTCs strongly correlates with cancer progression/regression and patient survival, and may antedate radiographic evidence of metastases.

The identification and characterization of CTCs is useful for early detection and treatment management of pre-metastatic and metastatic epithelial malignancies. For example, detection of CTCs in cancer patients is an effective tool for early diagnosis of primary or secondary cancer growth and for predicting the prognosis of cancer patients undergoing cancer therapies since the number and characterization of CTCs present in the blood of cancer patients has been correlated with overall prognosis and response to therapy. The ability to accurately detect CTCs is also an effective tool to monitor the course of treatment.

While numerous methods of detecting CTCs are known, there remains a need for therapeutically targeting CTCs with chemotherapeutic agents to reduce the viability of CTCs in a patient. Further, there is a need to remove CTC debris and excess chemotherapeutic reagents from extracorporeal blood caused by reducing the viability of CTCs.

SUMMARY

The invention relates to methods for therapeutically targeting circulating tumor cells during hemodialysis. In some embodiments, the method comprises the steps of (a) detecting circulating tumor cells from extracorporeal blood; (b) reducing the viability of the circulating tumor cells with a chemotherapeutic agent, wherein the step of reducing the viability of the circulating tumor cells generates circulating tumor cell debris and excess chemotherapeutic reagents; and (c) removing the circulating tumor cell debris and the excess therapeutic reagents via hemodialysis.

The circulating tumor cells can have an increased amount of intracellular lipid accumulation compared to the non-circulating tumor cells. The circulating tumor cells can have higher levels of lipid metabolism proteins compared to the non-circulating tumor cells. The viability of the circulating tumor cells may be reduced by suppressing lipid metabolism of the circulating tumor cells with a small interfering RNA (siRNA). The siRNA may be selected based on its interference with the expression of a specific gene encoding for a lipid metabolism protein, for example, acyl-CoA cholesterol acyltransferase 1 (ACAT1), adiponutrin, 1-acylglycerol-3-phosphate o-acyltransferase 2 (AGPAT2), adipose triglyceride lipase (ATGL), zinc-alpha-2-glycoprotein (AZGP1), cell death inducing DNA fragmentation factor proteins (CIDEA, CIDEB and CIDEC/FSP27), comparative gene idenfitication-58 (CGI-58), CTP phosphocholine cytidylyltransferase (CCT), acyl-CoA diacylglycerol acyltransferase (DGAT1 and DGAT2), hormone sensitive lipase (HSL), lipin1, PAT proteins, triacylglycerol hydrolase (TGH), fatty acid binding proteins (FABP 1-9), fatty acid transport proteins (FATP1-6), and acyl-CoA binding proteins (ACBPs).

The viability of the circulating tumor cells may be reduced by suppressing the lipid metabolism of the circulating tumor cells with a lipid metabolism inhibitor. For example, the lipid inhibitor may be selected based on targeting a lipid metabolism protein selected from the group consisting of acyl-CoA cholesterol acyltransferase 1 (ACAT1), adiponutrin, 1-acylglycerol-3-phosphate o-acyltransferase 2 (AGPAT2), adipose triglyceride lipase (ATGL), zinc-alpha-2-glycoprotein (AZGP1), cell death inducing DNA fragmentation factor proteins (CIDEA, CIDEB and CIDEC/FSP27), comparative gene idenfitication-58 (CGI-58), CTP phosphocholine cytidylyltransferase (CCT), acyl-CoA diacylglycerol acyltransferase (DGAT1 and DGAT2), hormone sensitive lipase (HSL), lipin1, PAT proteins, triacylglycerol hydrolase (TGH), fatty acid binding proteins (FABP 1-9), fatty acid transport proteins (FATP1-6), and acyl-CoA binding proteins (ACBPs).

The circulating tumor cells may exhibit protein hyperacetylation profiles.

The viability of the circulating tumor cells may be reduced by administration of a pharmaceutically acceptable post-translational modification preparation comprising glucosamine, resveratrol, and uridine.

The viability of the circulating tumor cells may be reduced by application of a localized electric field via electroporative flow cytometry. Side effects may be decreased.

The viability of the circulating tumor cells may be reduced by suppressing lipid metabolism of the circulating tumor cells with a small interfering RNA, administering a pharmaceutically acceptable post-translational modification preparation comprising glucosamine, resveratrol and uridine, and applying a localized electric field via electroporative flow cytometry.

BRIEF DESCRIPTION OF THE DRAWINGS

To understand the present disclosure, it will now be described by way of example, with reference to the accompanying drawings in which embodiments of the disclosures are illustrated and, together with the descriptions below, serve to explain the principles of the disclosure.

FIGS. 3A and 3B are graphs showing a comparison of elevated expression levels of lipid metabolism proteins in LNCaP prostate cancer cells compared to peripheral mononucleated blood cells (PBMC). FIG. 3A shows gene expression levels of fatty acid transport proteins (CLC27A1, 2, 4, 5) and fatty acid binding protein (FABP6). FIG. 3B shows protein expression levels of adipose triglyceride lipase (ATGL), acetyl-CoA acetyltransferase (ACAT1), 1-acylglycerol-3-phosphate O-acyltransferase (CGI-58), diglyceride acyltransferase 1 (DGAT1).

FIG. 4A is a time lapse image and FIGS. 4B and 4C are graphical representations of the nucleus expansion of a lung cancer cell under an applied electrical field. Time lapse images of simultaneous CARS imaging of a cancer cell membrane and two-photon fluorescence imaging of Hoechst 33342-stained nucleus. The nucleus expanded and retracted as a function of electric field intensity shown in FIG. 4B. FIG. 4B shows electric field intensity as a function of time. FIG. 4C shows normalized nucleus diameter of a cancer cell shown in (A) as a function of electric field intensity shown in (B) over time.

FIG. 5A is a time lapse image and FIG. 5B is a graphical representation of the selective killing of lung CTCs in whole blood samples with applied electrical fields. A lung CTC (arrow) expanded rapidly in a microfluidic channel with electric field intensity of 400 V/cm. No significant expansion of white blood cells or red blood cells was observed. FIG. 5B shows percentage of cell death as a function of applied electric field intensity. White blood cells (WBC), red blood cells (RBC). Error bars are standard deviation across triplicate experiments.

DETAILED DESCRIPTION

Figure 1:
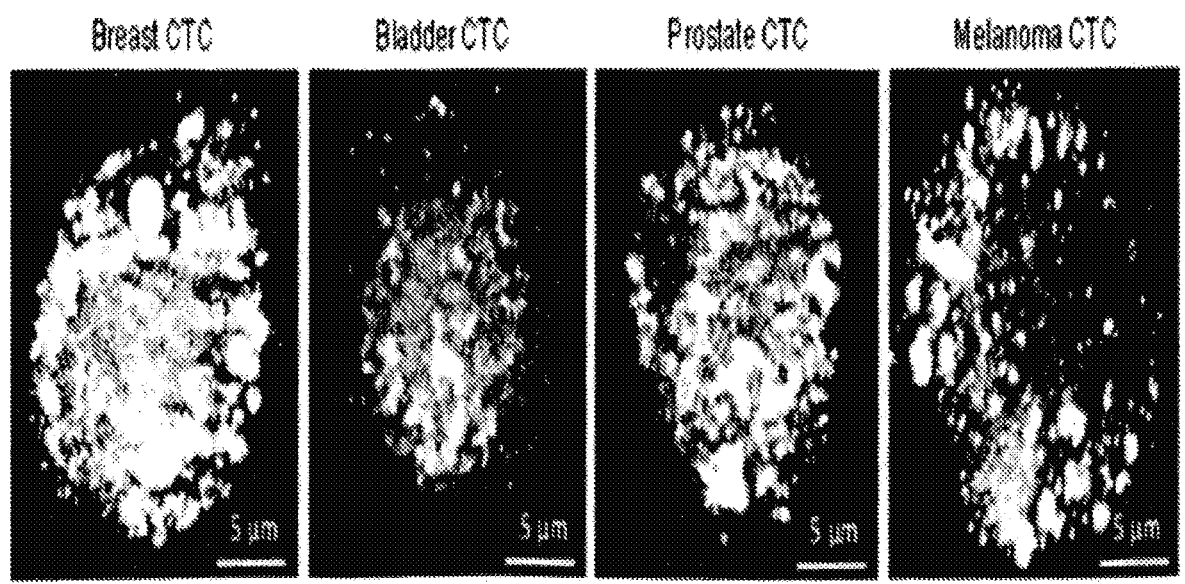
FIG. 1 is a comparison of lipid-rich CTCs isolated from the peripheral blood of breast, bladder, prostate and skin cancer patients. Images were taken with coherent anti-Stokes Raman scattering (CARS) microscopy at 2851 cm$^{-1}$ to probe for $CH_2$ vibration.

The present invention relates generally to cancer diagnostics and therapy, and more specifically to methods for therapeutic targeting of CTCs during hemodialysis. More particularly, the present invention is directed to a method for detecting and reducing the viability of CTCs with chemotherapeutic agents during hemodialysis. Elimination of CTCs from the bloodstream reduces cancer metastasis and increases survivability of cancer patients. Another advantage of the method described herein is the reduction in side effects for patients undergoing chemotherapy treatment.

The present invention is directed to a combinatorial approach for selectively killing CTCs during hemodialysis while leaving the viability of blood cells unaffected. The present invention is directed to a three-pronged approach to CTC elimination that includes: (1) suppression of expression level and enzymatic activity of lipid metabolism proteins with siRNAs and inhibitors to reduce CTC viability; (2) suppression of protein lysine acetylation with a post-translational modification ("PTM") preparation or "cocktail" to reduce CTC viability; and (3) application of localized electric fields to induce CTC cell death and enhance CTC uptake of chemotherapeutic agents. Such therapeutic procedures are conducted in the extracorporeal blood of cancer patients either simultaneously, sequentially, individually or in combination. Excess chemotherapeutic reagents and CTC debris are removed via dialysis. Consequently, side effects are expected to be minimal because cancer patients are not exposed to chemotherapeutic reagents or localized electric fields.

Diseases or other medical conditions for which the invention described herein are applicable include, but are not limited to, any of a variety of cancers or other neoplastic conditions. This includes, for example, epithelial cell cancers such as lung, ovarian, cervical, endometrial, breast, brain, colon and prostate cancers. Also included are gastrointestinal cancer, head and neck cancer, non-small cell lung cancer, cancer of the nervous system, kidney cancer, retina cancer, skin cancer, liver cancer, pancreatic cancer, genitalurinary cancer, bladder cancer, melanoma and leukemia. In addition, the methods of the present invention are equally applicable to detection, diagnosis and treatment of non-malignant tumors in an individual (e.g., neurofibromas, meningiomas, and schwannomas).

Definitions

The term "circulating tumor cell" (CTC) is intended to mean any circulating cancer cell that is found in a sample obtained from a subject. Typically, CTCs have been shed from a solid tumor. As such, CTCs are often epithelial cells shed from solid tumors that are found in very low concentrations in the circulation of patients with advanced cancers. CTCs may also be mesothelial cells from sarcomas or melanocytes from melanomas.

The term "early stage cancer" as used herein refers to those cancers which have been clinically determined to be organ-confined. Also included are tumors too small to be detected by conventional methods such as mammography for breast cancer patients, or X-rays for lung cancer patients. While mammography can detect tumors having approximately $2 \times 10^8$ cells, the methods of the present invention should enable detection of CTCs from tumors approximately this size or smaller.

The term "subject" as used herein refers to any individual or patient from whom CTCs (or a sample containing CTCs) is obtained or to whom the subject methods are performed. Generally the subject is human, although the subject may be an animal, including mammals such as rodents (including mice, rats, hamsters and guinea pigs), cats, dogs, rabbits, farm animals including cows, horses, goats, sheep, pigs, and primates (including monkeys, chimpanzees, orangutans and gorillas).

Methods

The present invention exploits the differences between CTCs and PBMCs to selectively kill CTCs while leaving PBMCs unharmed. To avoid side effects, which are inherent to most chemotherapeutic treatments, the present invention targets CTCs during hemodialysis procedures. Consequently, subjects are not exposed to excess drugs or therapeutic agents during treatment because they are removed from the blood via dialysis prior to blood returning to subject's body.

In one aspect, the invention relates to methods for therapeutically targeting CTCs during hemodialysis. Accordingly, in one embodiment the method comprises detecting CTCs from extracorporeal blood, reducing the viability of the CTCs, and removing the resulting CTC debris and excess therapeutic reagents via dialysis.

Figure 2:
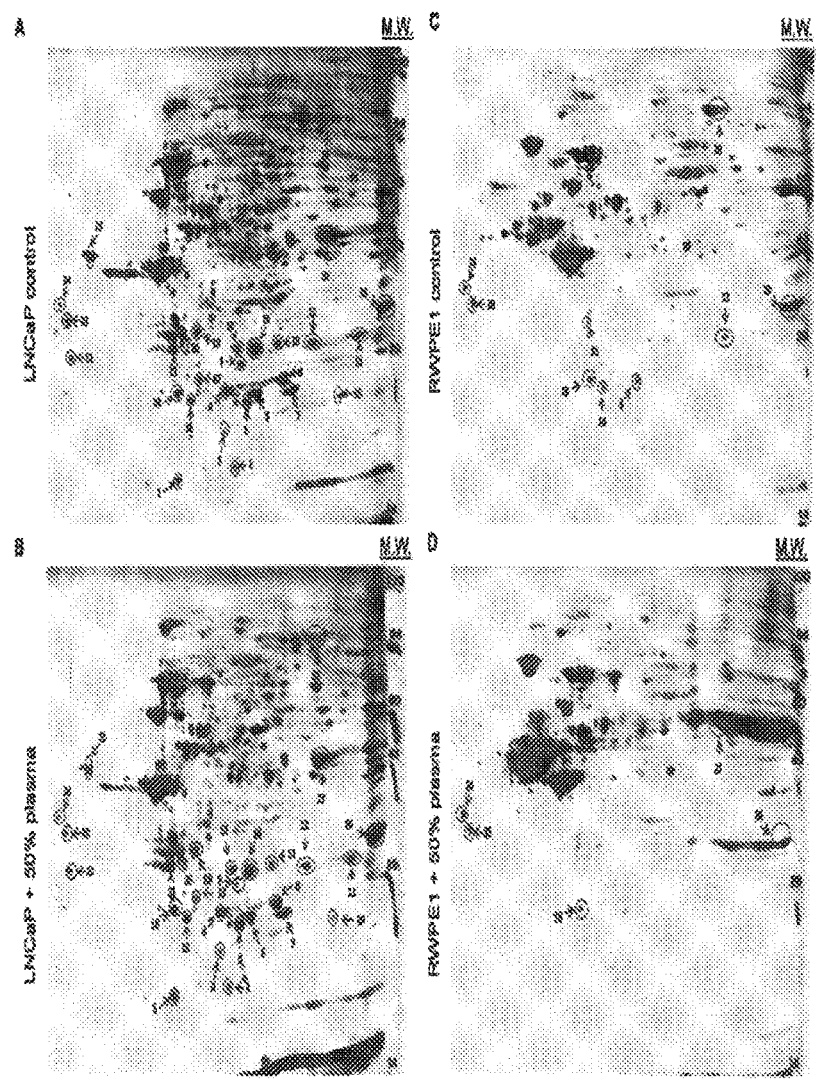
FIG. 2 is a comparison of 2D Western blots of protein lysine acetylation profiles of LNCaP cells ((A) untreated and (B) incubated with human plasma) and RWPE1 cells ((C) untreated and (D) incubated with human plasma).

Several molecular properties are unique to metastatic cancer cell lines and CTCs. First, CTCs exhibit high intracellular lipid droplet accumulation (FIG. 1). Second, metastatic prostate cancer cells express high levels of lipid metabolism proteins (FIG. 3). Third, metastatic prostate cancer cells exhibit hyper-acetylation of metabolic proteins that are insensitive to the nutrient status of the culturing media (FIG. 2). And fourth, metastatic lung cancer cells are susceptible to nucleus expansion and cell death induced by applied electric fields (FIGS. 4 and 5). These unique molecular properties are useful for therapeutic targeting of CTCs.

The extracorporeal blood containing CTCs may be obtained from any suitable source, such as from a sample taken or obtained from a subject, from a frozen stock, and the like. In preferred embodiments, the extracorporeal blood containing CTCs is obtained in a sample taken from a subject. There are several known methods and techniques available for detecting CTCs. A number of known methods of CTC detection are described in U.S. Patent Application 2013/0078667, which is incorporated herein by reference.

Intracellular lipid content is another method for detecting CTCs. Cancer cells (e.g., metastatic melanoma and prostate cancer cells) differ markedly from circulating leukocytes based on their intracellular lipid content. For example, CTCs contain lipid-rich structures, which are intracellular lipid droplets, but leukocytes generally do not. Furthermore, red blood cells, erythrocytes, platelets, and thrombocytes do not have intracellular lipid droplets. Thus, CTCs can be clearly detected from the blood based on intracellular lipid content. The ability to detect and characterize CTCs has the potential to aide in the diagnostic and individualized treatment of cancer subjects (e.g., personalized medicine). Intracellular lipid accumulation in non-adipocyte is generally accepted as a protective mechanism against lipotoxicity. As shown in FIG. 1, CTCs of multiple origins including lung, breast, bladder, prostate and melanoma are lipid rich. Cancer cells have a strong affinity for lipids and exhibit high lipid droplet accumulation following incubation with lipid-rich media. Most notably, increased intracellular lipid accumulation has been observed together with increased cancer aggressiveness. Lipid-rich CTCs are a consequence of malignant transformation and exposure to excess lipids in blood plasma.

Following detection, multiple approaches can be employed to selectively target CTCs and reduce the viability of the CTCs, including for example: (1) suppression of expression levels and enzymatic activity of lipid metabolism proteins with small interfering RNAs ("siRNAs") and inhibitors; (2) suppression of protein lysine acetylation with a post-translational modification (PTM) cocktail; and (3) application of localized electric fields to increase CTC uptake of therapeutic agents and induce CTC death. These approaches can be performed simultaneously, sequentially, individually, or in combination. CTCs can be targeted with therapeutic reagents and localized electric fields in extracorporeal bloods of cancer subjects.

In one embodiment of the present invention, siRNAs target lipid metabolism proteins to reduce CTC viability. By interfering with the expression level and enzymatic activity of lipid metabolism proteins, CTCs become sensitive to plasma lipotoxicity or are unable to meet the energy demands necessary for cell survival and growth.

Lipid metabolism proteins that are considered targets for siRNA interference may include, for example, Acyl-CoA cholesterol acyltransferase 1 (ACAT1)—an enzyme that catalyzes the formation of cholesterol esters using cholesterol and fatty acyl CoA as substrates; Adiponutrin—a patatin-like phospholipase domain-containing protein 3 that has triglyceride lipase and acylglycerol O-acyltransferase activities; 1-Acylglycerol-3-phosphate O-acyltransferase 2 (AGPAT2)—an enzyme that catalyzes triglyceride synthesis by using 1-acylglycerol-3 phosphate and fatty acyl CoA as substrates; Adipose triglyceride lipase (ATGL)—an enzyme that catalyzes the initial step in triglyceride hydrolysis into diacylglycerol; Zinc-alpha-2-glycoprotein (AZGP1)—an enzyme that stimulates lipid degradation in adipocytes and causes the extensive fat losses associated with some advanced cancers; Cell Death Inducing DNA Fragmentation Factor proteins (CIDEA, CIDEB, & CIDEC/FSP27)—a family of three proteins that promote lipid droplet growth; Comparative gene identification-58 (CGI-58)—a co-activator of ATGL that participates in lipolysis; CTP phosphocholine cytidylyltransferase (CCT)—a rate limiting enzyme for phosphatidylcholine synthesis; Acyl-CoA:diacylglycerol acyltransferases (DGAT1 & DGAT2)—two proteins that catalyze triglyceride synthesis by combining diacylglycerol and fatty acyl CoA; Hormone sensitive lipase (HSL)—an enzyme that catalyzes the conversion of diacylglycerol into monoacylglycerol; Lipin1—a phosphatidate phosphatase which catalyzes the conversion of phosphatidic acid to diacyiglycerol for triglyceride synthesis; PAT proteins—a family of lipid droplet proteins including Perilipin 1, Perilipin2/adipophilin (ADRP), Perilipin3/TIP47, Perilipin4/S3-12, Perilipin 5 (OXPAT), PAT proteins regulate lipid droplet biogenesis and growth; Triacylglycerol hydrolase (TGH)—an enzyme that hydrolyzes triglyceride; Fatty acid binding proteins (FABP 1-9)—a family of transport proteins for fatty acids, eicosanoids, and retinoids; Fatty acid transport proteins (FATP1-6)—transmembrane solute carrier family 27 (SLC27) proteins that enhance the uptake of long chain and very long chain fatty acids into cells; and Acyl-CoA binding proteins (ACBPs)—a small carrier protein for medium and long-chain acyl-CoA esters.

In some embodiments, the CTCs may have an increased amount of intracellular lipid accumulation compared to the non-circulating tumor cells. In some embodiments, the CTCs may have higher levels of lipid metabolism proteins compared to the non-CTCs.

Inhibitors to the aforementioned lipid metabolism proteins may be employed to inhibit their enzymatic activities and reduce CTC viability in plasma. The lipid inhibitor may be selected based on targeting a lipid metabolism protein selected, for example, from the group consisting of acyl-CoA cholesterol acyltransferase 1 (ACAT1), adiponutrin, 1-acylglycerol-3-phosphate o-acyltransferase 2 (AGPAT2), adipose triglyceride lipase (ATGL), zinc-alpha-2-glycoprotein (AZGP1), cell death inducing DNA fragmentation factor proteins (CIDEA, CIDEB and CIDEC/FSP27), comparative gene idenfitication-58 (CGI-58), CTP phosphocholine cytidylyltransferase (CCT), acyl-CoA diacylglycerol acyltransferase (DGAT1 and DGAT2), hormone sensitive lipase (HSL), lipin1, PAT proteins, triacylglycerol hydrolase (TGH), fatty acid binding proteins (FABP 1-9), fatty acid transport proteins (FATP1-6), and acyl-CoA binding proteins (ACBPs).

In another embodiment, protein lysine acetylation is suppressed with a post-translational modification cocktail to reduce CTC viability. A post-translational modification (PTM) preparation or cocktail is used to suppress protein hyper-acetylation in cancer cells. The post-translational modification cocktail may comprise, for example, glucosamine, resveratrol, and uridine. The PTM cocktail may also include, additionally or alternatively, deacetylase activators such as histone deacetylase (HDAC) activators or Sir2-like family deacetylase activators. The PTM cocktail or pharmaceutically acceptable preparation thereof can be used as a potent therapy against protein hyper-acetylation of cancer cells. The PTM preparation may restore nutrient sensing of cancer cells and sensitize cancer cells to plasma toxicity. A PTM preparation may reduce LNCaP viability in the absence or presence of plasma incubation.

Protein hyper-acetylation and impaired nutrient sensing can be used to target CTCs. Protein acetylation and glycosylation are nutrient-sensitive post-translational modifications. Therefore, reducing protein acetylation levels restores nutrient sensing of cancer cells and in turn sensitizes them to plasma toxicity.

Resveratrol promotes protein lysine deacetylation via activation of sirtuin deacetylases. Resveratrol is a polyphenol compound found in the skins of grapes, blueberries, raspberries, and mulberries. Resveratrol was identified to be a chemopreventive agent for skin cancer. Resveratrol enhances binding and deacetylation of peptide substrates by sirtuin deacetylases. Therapeutic potentials of resveratrol in rodent models of stress and disease have been widely demonstrated. Resveratrol has the potential for reducing protein lysine C acetylation profiles in cancer cells by activating sirtuin deacetylases.

Uridine and glucosamine promote protein glycosylation and suppress lysine acetylation. The combination of uridine and glucosamine administration is known to promote protein glycosylation via the production of UDP-N-acetylglucosamine (UDP-GlcNAc).

In another embodiment, application of localized electric fields is used to induce CTC cell death and enhance CTC uptake of chemotherapeutic agents. In one aspect, electroporation is utilized to promote gene delivery, drug uptake, and cancer cell ablation.

The present invention utilizes localized electric fields to induce CTC cell death and enhance CTC uptake of therapeutic agents. Pulsed or constant electric fields at electric field strengths from 5 mV/cm to 5000 V/cm may be used. For example, the electric field strength may be about 5 mV/cm, about 50 mV/cm, about 100 mV/cm, about 500 mV/cm, about 1 V/cm, about 10 V/com, about 100 V/cm, about 1000 V/cm, about 2500 V/com, or about 5000 V/cm. The electric field may be applied for a duration from 1 microsecond to 10 hours. For example, the duration of electric field application may be about 1 microsecond, about 10 microseconds, about 100 microseconds, about 1 second, about 1 minute, about 1 hour, about 5 hours, or about 10 hours. Pulsed or constant electric fields at an effective strength and for an effective duration may be applied at the conductive tubing section in order to: (1) selectively kill CTCs while leaving the viability of other blood cells unaffected; and (2) enhance delivery of siRNAs and other therapeutic agents into CTCs.

Electrical signals play an important role in the regulation of cell division, migration, and differentiation. Electrical impulse and potential are associated with critical physiological processes such as muscle contraction, neurotransmission, hearing, and organogenesis. Application of external electrical signals has been shown to promote contraction of cardiac muscle, regeneration of damage spinal nerves, neuronal migration, and wound healing. In addition, deep brain stimulation is a therapy that uses electrical stimulation to treat Parkinson's disease. Electrical signals, together with biochemical and molecular signals, control vital aspects of biological systems in health and disease. Electrochemotherapy is a therapeutic approach to cancer treatment that combines anti-cancer agents with high electrical voltage to target solid tumors. Electroporation via application of electrical fields alone is also successful at disrupting cancer cell replication in animal xenograft models with a wide range of human tumors. Application of electric fields by themselves or together with chemotherapeutic agents has been demonstrated to be an effective means for the treatment of solid tumors. The present invention provides application of electric fields to kill CTCs directly via nucleus expansion or indirectly via increased delivery efficiency of siRNAs and chemotherapeutic agents into CTCs.

Figure 6:
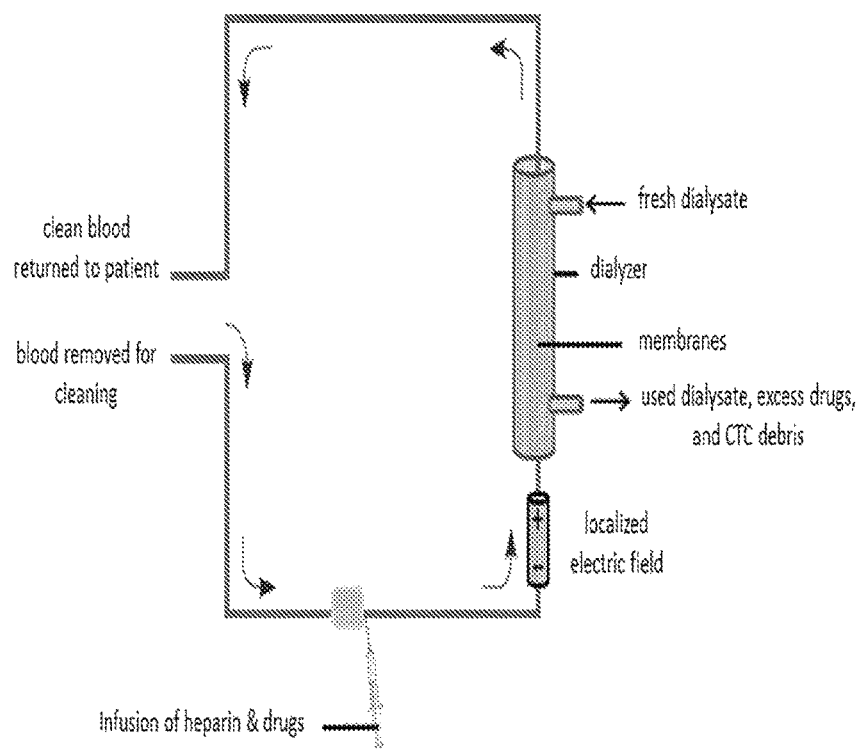
FIG. 6 is a schematic showing therapeutic targeting of CTCs during hemodialysis. CTC in extracorporeal blood are exposed to drugs (therapeutic agents) and localized electric fields. Excess drugs are removed from blood via dialysis prior to clean blood being returned to patients.

Hemodialysis is a procedure to remove waste products from extracorporeal blood when the kidneys are failing to perform their physiological function. In hemodialysis, counter current flows between dialysate and extracorporeal blood are separated by a semi-permeable membrane. Waste products of metabolism in the blood move across the semi-permeable membrane into dialysate from high concentration to low concentration. In 2009, 380,760 patients with renal failure received hemodialysis in the US. Hemodialysis presents an opportunity to therapeutically target CTCs with minimal exposure of human body to therapeutic agents. As outlined in FIG. 6, therapeutic agents and localized electric field are introduced to extracorporeal blood to target CTCs. Excess therapeutic agents and CTC debris are removed from blood via dialysis. Patients are not exposed to therapeutic agents or localized electric field.

The content of each of the patents, patent applications, patent publications and published articles cited in this specification are herein incorporated by reference in their entirety.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLES

1. Suppression of Expression Level and Enzymatic Activity of Lipid Metabolism Proteins with siRNAs and Inhibitors to Reduce CTC Viability.

Figure 7:
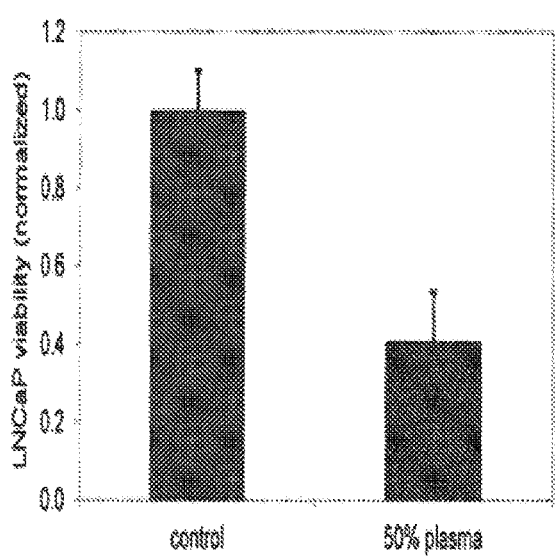
FIG. 7 is a graphical representation comparing toxicity of plasma to metastatic prostate cancer LNCaP cells. Incubation with 50% plasma for 24 hours leads to a reduction of nearly 60% in cell viability. Error bars are standard deviation of triplicate experiments. Cell viability was determined using commercial MTS assays according to manufacturer's protocols.

The high lipid content of plasma is generally toxic to cells other than blood cells and vascular endothelial cells (FIG. 7). The ability of CTCs to survive in the bloodstream is likely due to high expression levels of lipid metabolism proteins (FIG. 3). Lipid metabolism proteins channel excess lipids into neutral cytoplasmic lipid droplets and suppress lipotoxic effects of the plasma on CTCs. Lipid metabolism proteins also mobilize lipids from lipid droplets for cellular energy metabolism and for membrane phospholipid biosynthesis for cell survival and growth.

Impaired energy metabolism and nutrient-sensing of cancer cells is a well-known phenomenon. Nutrient sensing in prostate cancer cells has been examined by observing protein lysine acetylation profiles as a function of incubation with nutrient-rich plasma. LNCaP prostate metastatic cancer cells exhibit hyper-acetylation of low molecular weight proteins compared to RWPE1 non-transformed prostate epithelial cells. Following plasma incubation, protein lysine acetylation profiles are unchanged for LNCaP cells while being significantly altered for RWPE1 cells (FIG. 2). Protein lysine acetylation is another means of cellular nutrient sensing and signaling and therefore useful in detecting CTCs. Unchanged protein lysine acetylation profiles of LNCaP cells following incubation with nutrient-rich plasma indicate impaired nutrient sensing.

Increased lipogenesis in cancer cells is a well observed event. Increased expression levels of lipid metabolism proteins critical for fatty acid biosynthesis, catabolism, and transport have also been observed in CTCs (FIG. 3). Inhibiting lipogenesis in cancer cells has been shown to induce cancer cell death. Consequently, enzymes involved in lipid metabolism are potent targets for anti-cancer therapy.

Figure 8:
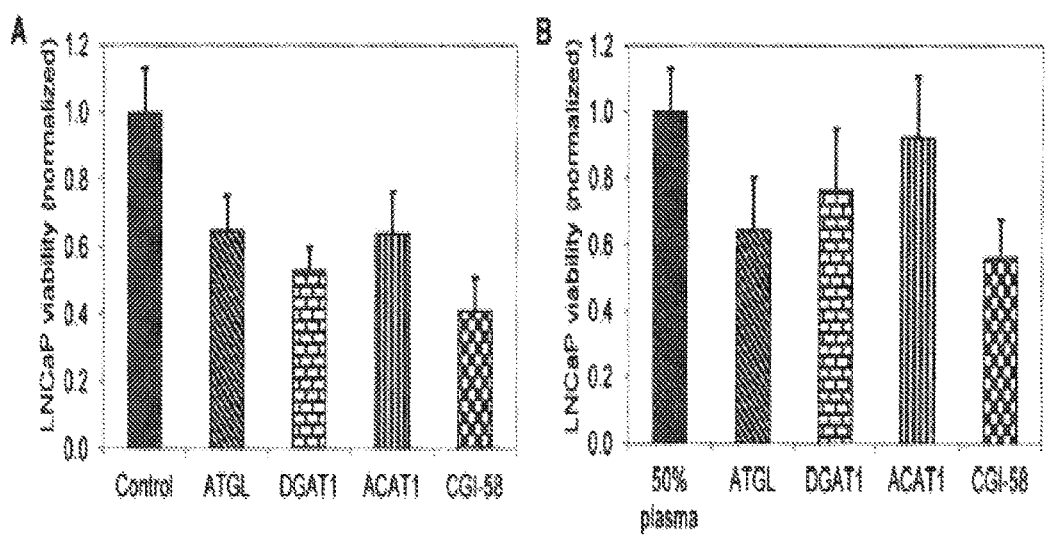
FIGS. 8A and 8B are graphical representations of siRNA targeting of lipid metabolism proteins in reducing LNCaP viability. LNCaP viability as a function of siRNA targeting ATGL, DGAT1, ACAT1, and CGI-58 in growth media (A) and growth media supplemented with 50% plasma (B) is shown.
Figure 9:
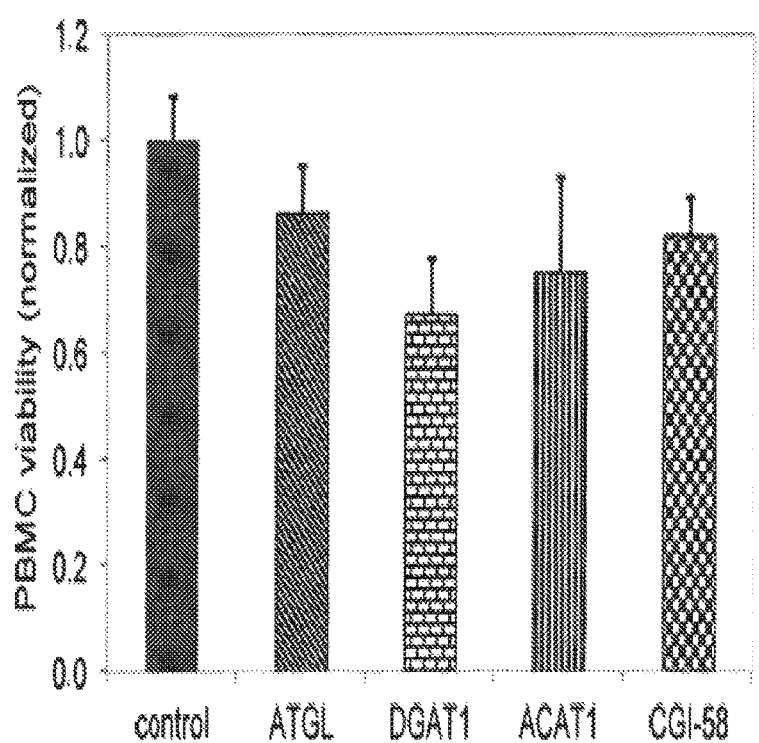
FIG. 9 is a graphical representation of siRNA targeting of lipid metabolism proteins having a minimal effect on PBMC viability. PBMC viability is shown as a function of siRNA targeting of ATGL, DGAT1, ACTA1, and CGI-58. Error bars are standard deviation of triplicate experiments.

As demonstrated in FIG. 8, siRNAs interfered with the expression of ATGL, ACAT1, DGAT1, and CGI-58, which lead to significant reduction of LNCaP cell viability in the absence or presence of plasma incubation. However, siRNA targeting of lipid metabolism proteins had minimal impact on PBMC viability. While reducing LNCaP viability by up to 60%, siRNA targeting of lipid metabolism proteins had milder effects on PBMC viability. On average, siRNA interference reduced PBMC viability by 20-30% (FIG. 9). Therefore, siRNA targeting of lipid metabolism proteins can be used to selectively kill CTC while causing minimal effects on PBMC.

2. Suppression of Protein Lysine Acetylation with a Post-Translational Modification Cocktail to Reduce CTC Viability.

Metastatic prostate cancer cells exhibited protein hyper-acetylation profiles compared to non-transformed prostate epithelial cells (FIG. 2). Protein hyper-acetylation profiles of cancer cells, which remained unchanged following incubation with 50% plasma, indicated impairment in the nutrient signaling pathway. Reducing protein acetylation level may restore nutrient sensing of cancer cells and sensitize them to plasma toxicity.

Figure 10:
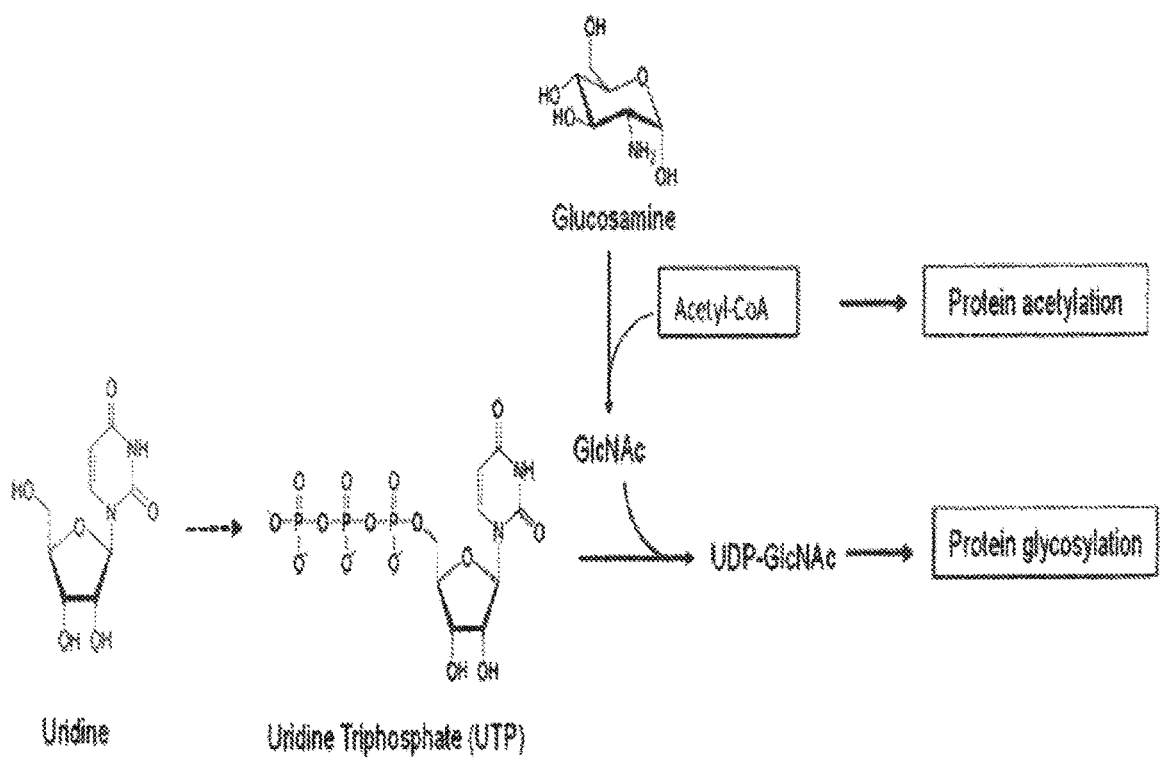
FIG. 10 is a schematic showing uridine and glucosamine promote protein glycosylation and suppress protein acetylation.

It has been discovered that uridine administration promotes protein glycosylation and suppresses lysine acetylation. The formation of UDP-GlcNAc draws acetyl-CoA away from protein acetylation (FIG. 10). Increases in UDP-GlcNAc bioavailability non-specifically promote protein O-linked glycosylation.

Figure 11:
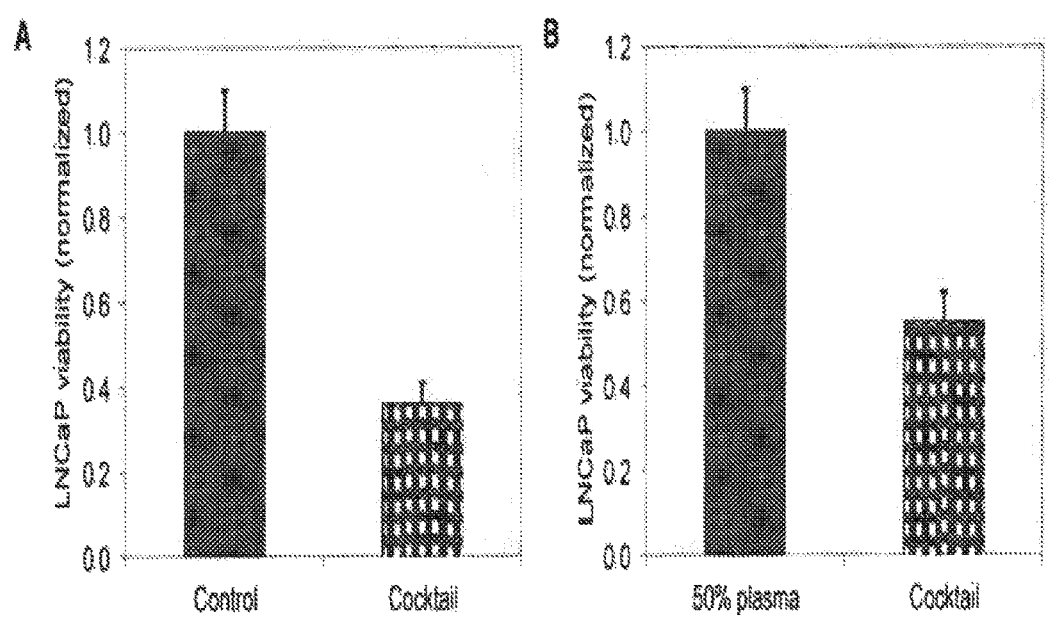
FIGS. 11A and 11B are graphical representations of the effects of a post-translational modification preparation in reducing LNCaP viability in the absence (A) or presence (B) of plasma. Error bars are standard deviation of triplicate experiments.
Figure 12:
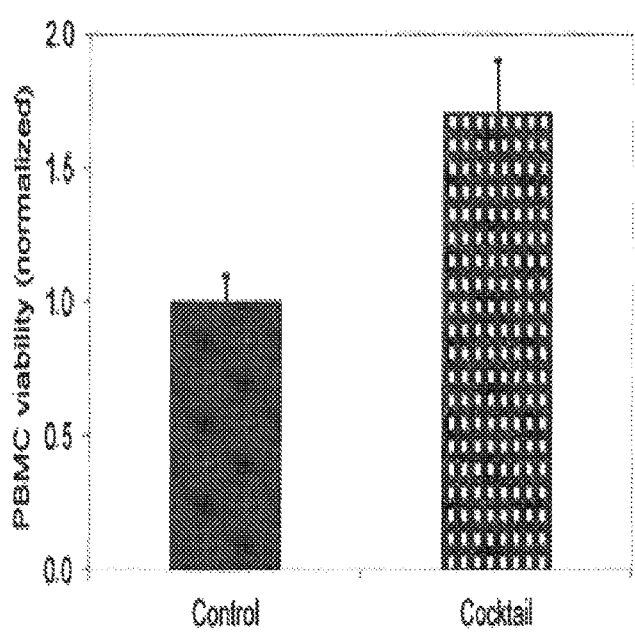
FIG. 12 is a graphical representation showing a post-translational modification (PTM) cocktail enhances PBMC viability. Error bars are standard deviation of triplicate experiments.

LNCaP cells were treated with a PTM cocktail comprising of 100 pM uridine, 10 mM glucosamine, and 50 pM resveratrol. It was discovered that the PTM cocktail reduced LNCaP viability by nearly 60% in the absence of plasma (FIG. 11). In contrast, the PTM cocktail reduced LNCaP viability by approximately 45% in the presence of 50% plasma. Noteworthy is that 50% plasma incubation alone reduced LNCaP viability by approximately 60%. The combination of 50% plasma and the PTM cocktail reduced LNCaP viability by as much as 80%. Thus, the PTM cocktail effectively reduced LNCaP viability in the absence or presence of plasma. Moreover, the PTM cocktail improved PBMC viability. Surprisingly, a PTM cocktail increased peripheral mononucleated cells (PBMC) viability by nearly 70% compared to untreated control (FIG. 12). Taken together, a PTM cocktail reduces LNCaP cells viability while enhancing PBMC viability.

3. Application of Localized Electric Fields to Induce CTC Cell Death and Enhance CTC Uptake of Therapeutic Agents Changes associated with nuclei structures and certain mechanics of cancer cells during malignant transformation are well-characterized and useful for detecting CTCs. Among such changes are enlarged nucleoli and increased plasticity of the nuclear shape. Enlarged nucleoli are associated with increased ribosome biogenesis and proliferation of cancer cells. Increased plasticity of nuclear shape is associated with cancer cell motility and invasion. Additionally, polyploidy is a frequent phenomenon leading to genomic instability, aneuploidy, and the development of cancer.

It has been observed that cancer nuclei exhibit rapid expansion under applied electric fields (FIG. 4). Such nucleus expansion of cancer cells is attributable to changes in the nuclei structures and mechanics such as enlarged nucleus, polyploidy, and increased plasticity of the nuclear envelope. In contrast, white blood cells (WBC) do not exhibit any measurable nucleus expansion under the same applied electric field. Red blood cells (RBC) are non-nucleated cells with the plasma membrane as the only structural component. Therefore, lung CTCs are clearly distinguishable from WBCs or RBCs in whole blood samples based on nucleus expansion under an applied electric field (FIG. 5).

It has also been observed that application of an electric field of 400 V/cm expanded the nucleus diameter of a lung CTC by 38% (FIG. 4). The effective electric field intensity to kill 50% of CTCs was 350 V/cm at 200 ms exposure duration (FIG. 5). At 350 V/cm and 200 ms exposure duration, less than 5% WBC cell death was observed with propidium iodide staining and 0% RBC cell death was evaluated with membrane integrity. Consequently, the present invention provides selective killing of CTCs in blood samples that is achieved with electroporation.

It was previously discovered that the use of an electroporative microfluidic chip could be used to selectively purge CTCs in flow. Besides the well-known effects of electric pulses on cell membrane pore formation, nucleus expansion of CTCs was observed (FIG. 4). Complete purging of CTCs during flow using localized electric fields left the viability of other blood cells minimally affected (FIG. 5). As a result, localized electric fields can be used to selectively purge CTCs in the bloodstream of cancer patients.

What is claimed is:

1. A method for therapeutically targeting circulating tumor cells during hemodialysis, the method comprising:
    detecting circulating tumor cells from extracorporeal blood;
    reducing the viability of the circulating tumor cells, wherein the viability of the circulating tumor cells is reduced by (1) applying a localized electric field via electroporative flow cytometry; (2) suppressing lipid metabolism of circulating tumor cells with a small interfering RNA (siRNA) or a lipid metabolism inhibitor, and (3) administering a pharmaceutically acceptable post-translational modification preparation comprising glucosamine, resveratrol, and uridine, wherein the step of reducing the viability of the circulating tumor cells generates circulating tumor cell debris and excess chemotherapeutic reagents; and
    removing the circulating tumor cell debris and the excess chemotherapeutic reagents via dialysis.

2. The method of claim 1, wherein the circulating tumor cells have an increased amount of intracellular lipid accumulation compared to the non-circulating tumor cells.

3. The method of claim 1, wherein the circulating tumor cells have higher levels of lipid metabolism proteins compared to the non-circulating tumor cells.

4. The method of claim 1, wherein the siRNA interferes with lipid metabolism proteins selected from the group consisting of acyl-CoA cholesterol acyltransferase 1 (ACAT1), adiponutrin, 1-acylglycerol-3-phosphate o-acyltransferase 2 (AGPAT2), adipose triglyceride lipase (ATGL), zinc-alpha-2-glycoprotein (AZGP1), cell death inducing DNA fragmentation factor proteins (CIDEA, CIDEB and CIDEC/FSP27), comparative gene idenfitication-58 (CGI-58), CTP phosphocholine cytidylyltransferase (CCT), acyl-CoA diacylglycerol acyltransferase (DGAT1 and DGAT2), hormone sensitive lipase (HSL), lipin1, PAT proteins, triacylglycerol hydrolase (TGH), fatty acid binding proteins (FABP 1-9), fatty acid transport proteins (FATP1-6), and acyl-CoA binding proteins (ACBPs).

5. The method of claim 1, wherein the target of the lipid metabolism inhibitor is selected from the group consisting of acyl-CoA cholesterol acyltransferase 1 (ACAT1), adiponutrin, 1-acylglycerol-3-phosphate o-acyltransferase 2 (AGPAT2), adipose triglyceride lipase (ATGL), zinc-alpha-2-glycoprotein (AZGP1), cell death inducing DNA fragmentation factor proteins (CIDEA, CIDEB and CIDEC/FSP27), comparative gene idenfitication-58 (CGI-58), CTP phosphocholine cytidylyltransferase (CCT), acyl-CoA diacylglycerol acyltransferase (DGAT1 and DGAT2), hormone sensitive lipase (HSL), lipin1, PAT proteins, triacylglycerol hydrolase (TGH), fatty acid binding proteins (FABP 1-9), fatty acid transport proteins (FATP1-6), and acyl-CoA binding proteins (ACBPs).

6. The method of claim 1, wherein the circulating tumor cells exhibit protein hyper-acetylation profiles.

7. The method of claim 1, wherein the pharmaceutically acceptable post-translational modification preparation further comprises a deacetylase activator.

8. The method of claim 1, wherein side effects are decreased.

9. The method of claim 1, further comprising applying a chemotherapeutic agent simultaneously, sequentially, individually or in combination with the method of reducing the viability of the circulating tumor cells.

10. The method of claim 1, wherein a localized electric field of 5 mV/cm to 5000 V/cm is applied.

* * * * *